United States Patent
Kostirev et al.

(10) Patent No.: US 10,831,864 B2
(45) Date of Patent: Nov. 10, 2020

(54) VISUAL COMPARISON OF DATA CLUSTERS

(71) Applicant: International Business Machines Corporation, Armonk, NY (US)

(72) Inventors: Igor Kostirev, Kibutz Adamit (IL); Alex Melament, Kiriat Mozkin (IL); Yardena Peres, Haifa (IL); Edward Vitkin, Nesher (IL); Bazarbek Uatay, Astana (KZ)

(73) Assignee: International Business Machines Corporation, Armonk, NY (US)

( * ) Notice: Subject to any disclaimer, the term of this patent is extended or adjusted under 35 U.S.C. 154(b) by 841 days.

(21) Appl. No.: 14/274,785

(22) Filed: May 12, 2014

(65) Prior Publication Data

US 2015/0324090 A1 Nov. 12, 2015

(51) Int. Cl.
*G06F 3/048* (2013.01)
*G06F 16/00* (2019.01)
(Continued)

(52) U.S. Cl.
CPC ........ *G06F 19/325* (2013.01); *G06F 3/04817* (2013.01); *G06F 3/04842* (2013.01);
(Continued)

(58) Field of Classification Search
CPC ........ G06F 19/325; G06F 19/00; G06F 16/00; G06F 3/04842; G06F 3/04817; G16H 15/00; G16H 70/20
See application file for complete search history.

(56) References Cited

U.S. PATENT DOCUMENTS 6,100,901 A    8/2000 Mohda et al.
7,665,064 B2 * 2/2010 Able ................ G06F 17/30861
                                                        717/117
(Continued)

OTHER PUBLICATIONS

Koop et al., "Visual Summaries for Graph Collections", IEEE Pacific Visualization Symposium, 2013.
(Continued)

*Primary Examiner* — Arpan P. Savla
*Assistant Examiner* — Haimei Jiang
(74) *Attorney, Agent, or Firm* — Dvir Gassner

(57) ABSTRACT

A method comprising using at least one hardware processor for: receiving multiple data clusters, each comprising one or more path variations of a process performed with respect to multiple subjects, wherein each of the path variations comprises multiple stages of the process, and wherein at least some of the stages, each comprises one or more parameters; constructing a visualization template representative of the path variations, wherein the visualization template comprises multiple nodes, each node having one or more graphical attributes, wherein each node representative of a corresponding stage; assigning each of the graphical attributes of each of the nodes to a corresponding parameter of the corresponding stage; and visualizing one or more differences between the data clusters by generating at least one instance of the visualization template, the instance being representative of and corresponding to at least two of the data clusters, wherein each of the at least one instance is representative of and corresponding to at least one of the data clusters, and wherein in the at least one instance, each of the assigned one or more graphical attributes of each node represent a value of the corresponding parameter, the value relating to the corresponding stage of the at least one corresponding data cluster.

10 Claims, 4 Drawing Sheets

(51) Int. Cl.
*G16H 15/00* (2018.01)
*G06F 19/00* (2018.01)
*G06F 3/0484* (2013.01)
*G06F 3/0481* (2013.01)
*G16H 70/20* (2018.01)

(52) U.S. Cl.
CPC .............. *G06F 16/00* (2019.01); *G06F 19/00* (2013.01); *G16H 15/00* (2018.01)

(56) References Cited

U.S. PATENT DOCUMENTS

| | | | | |
|---|---|---|---|---|
| 8,786,603 | B2* | 7/2014 | Rasmussen | G06T 11/206 345/440 |
| 9,501,540 | B2* | 11/2016 | Parker | G06F 17/30572 |
| 2003/0216939 | A1 | 11/2003 | Bito et al. | |
| 2005/0060287 | A1* | 3/2005 | Hellman | G06F 17/30705 |
| 2005/0091510 | A1* | 4/2005 | McKeon | G06F 9/451 713/185 |
| 2005/0122337 | A1* | 6/2005 | Chen | G06T 11/40 345/545 |
| 2006/0075505 | A1* | 4/2006 | Murthy | G06F 21/10 726/26 |
| 2009/0198725 | A1* | 8/2009 | Lee | G06F 17/30961 |
| 2011/0010267 | A1* | 1/2011 | Devries | G06Q 30/0607 705/26.25 |
| 2011/0060704 | A1* | 3/2011 | Rubin | G06N 99/005 706/12 |
| 2012/0021355 | A1 | 8/2012 | Schoenberg et al. | |
| 2012/0220276 | A1* | 8/2012 | Kobylarz | H04W 4/00 455/414.1 |
| 2013/0185231 | A1* | 7/2013 | Baras | G06F 19/3437 706/12 |
| 2013/0282889 | A1* | 10/2013 | Tito | H04L 43/00 709/224 |
| 2013/0339643 | A1* | 12/2013 | Tekade | G06F 17/30581 711/162 |
| 2015/0019569 | A1* | 1/2015 | Parker | G06F 17/30572 707/748 |

OTHER PUBLICATIONS

Streit et al., "Model-Driven Design for the Visual Analysis of Heterogeneous Data", IEEE Transactions on Visualization and Computer Graphics, vol. 18, No. 6, Jun. 2012.
Allan et al., "Strategy-based Interactive Cluster Visualization for Information Retrieval", International Journal on Digital Libraries, Aug. 2000, vol. 3, Issue 2, pp. 170-184.
Merkl et al., "Alternative Ways for Cluster Visualization in Self-Organizing Maps", In: Proceedings of the Workshop on Self-Organizing Maps (WSOM'97), Finland, Jun. 1997, pp. 106-111.
Shi et al., "Path line attributes-an information visualization approach to analyzing the dynamic behavior of 3d time-dependent flow fields", Topology-Based Methods in Visualization II, Mathematics and Visualization 2009, pp. 75-88.
Saraiya et al., "An Insight-Based Longitudinal Study of Visual Analytics", IEEE Transactions on Visualization and Computer Graphics, vol. 12, No. 6, 2006.
Plaisant et al., "Life Lines: using visualization to enhance navigation and analysis of patient records", In Proceedings of the 1998 American Medical Informatic Association Annual Fall Symposium.
Shahar et al., "Distributed, intelligent, interactive visualization and exploration of time-oriented clinical data and their abstractions", Journal of Artificial Intelligence in Medicine, vol. 38 Issue 2, 2006, pp. 115-135.
Callahan et al., "VisTrails: visualization meets data management", SIGMOD '06 Proceedings of the 2006 ACM SIGMOD international conference on Management of data, pp. 745-747.
Van Wijk et al., "Cluster and calendar based visualization of time series data", IEEE Symposium on Information Visualization (INFOVIS'99), pp. 4-9, Oct. 1999.
Daniel A. Keim, "Information visualization and visual data mining", IEEE Transactions on Visualization and Computer Graphics, vol. 7 Issue 1, Jan. 2002.

* cited by examiner

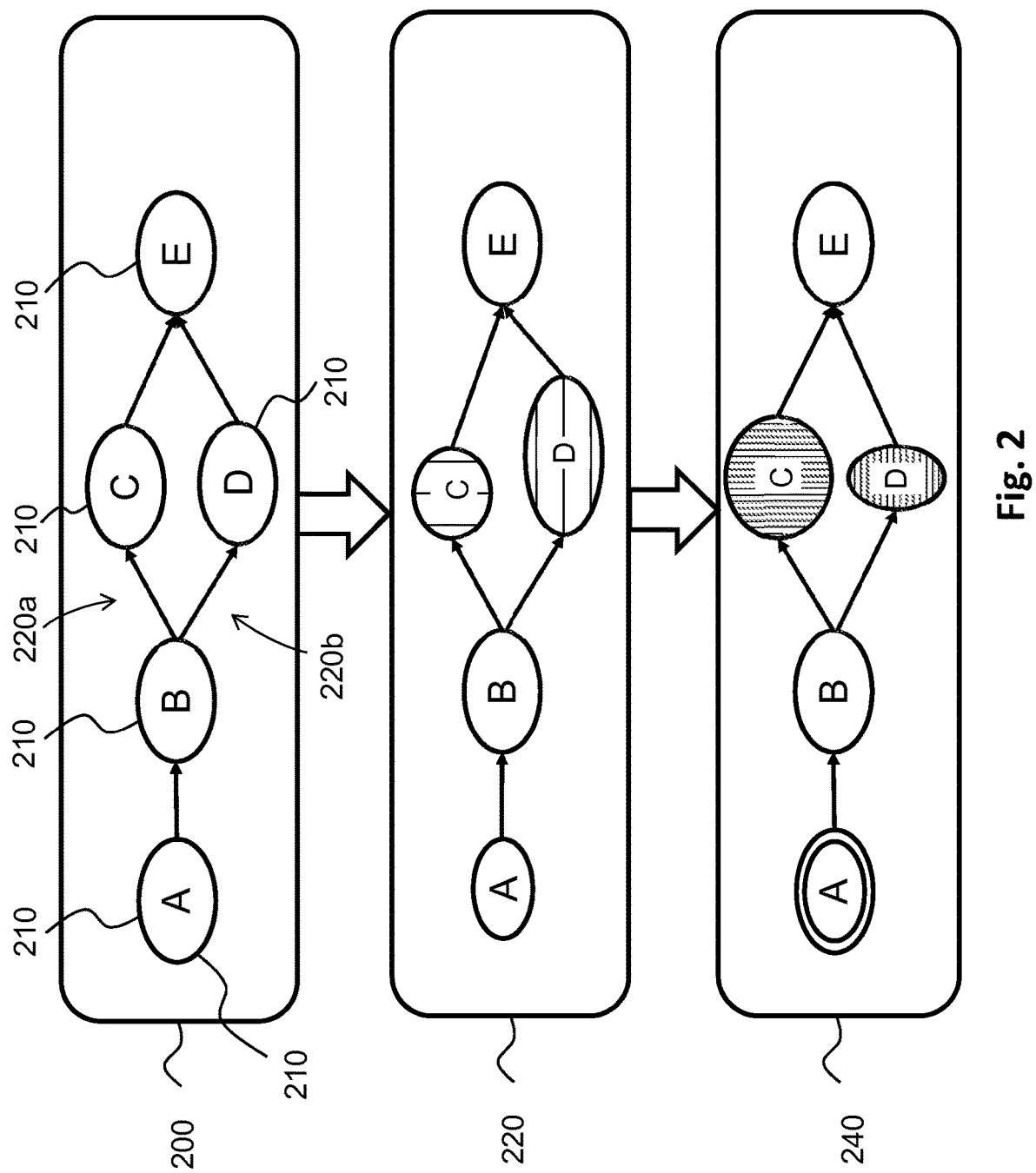

VISUAL COMPARISON OF DATA CLUSTERS

BACKGROUND

The present invention relates to the field of information visualization.

Study of processes in various fields, such as medical treatment processes, requires processing and visualization of growing amounts of data. Existing clustering algorithms are utilized for processing of such process data. However, the visualization is more of a challenge, because it requires deep understanding of the process itself, often leading to customization of visualization for each process type.

During study of various processes, a researcher is expected to perform clustering of the available data. Once the data is clustered, the results should be interpreted by the researcher to make some study conclusion. Such interpretation should be done in the context of the studied process. There is a clear need for tools enabling visual analysis and comparison of the received clustering results. To be meaningful to the end user, such tools should represent the clustering findings in the process context.

The foregoing examples of the related art and limitations related therewith are intended to be illustrative and not exclusive. Other limitations of the related art will become apparent to those of skill in the art upon a reading of the specification and a study of the figures.

SUMMARY

The following embodiments and aspects thereof are described and illustrated in conjunction with systems, tools and methods which are meant to be exemplary and illustrative, not limiting in scope.

There is provided, in accordance with an embodiment, a method comprising using at least one hardware processor for: receiving multiple data clusters each comprising one or more path variations of a process performed with respect to multiple subjects, wherein each of said one or more path variations comprises multiple stages of said process, and wherein at least some of said multiple stages each comprises one or more parameters; constructing a visualization template representative of said path variations of said process, wherein said visualization template comprises multiple nodes, each node having one or more graphical attributes, wherein each node representative of a corresponding stage of said multiple stages; assigning each of said one or more graphical attributes of each of said nodes to a corresponding one of said one or more parameters of said corresponding stage; and visualizing one or more differences between said data clusters by generating at least one instance of said visualization template, said at least one instance being representative of and corresponding to at least two of said data clusters, wherein each of said at least one instance is representative of and corresponding to at least one of said data clusters, and wherein in said at least one instance, each of said assigned one or more graphical attributes of each node represent a value of said corresponding one of said one or more parameters, said value relating to said corresponding stage of said at least one corresponding data cluster.

There is further provided, in accordance with an embodiment, a computer program product comprising a non-transitory computer-readable storage medium having program code embodied therewith, the program code executable by at least one hardware processor to: receive multiple data clusters each comprising one or more path variations of a process performed with respect to multiple subjects, wherein each of said one or more path variations comprises multiple stages of said process, and wherein at least some of said multiple stages each comprises one or more parameters; construct a visualization template representative of said path variations of said process, wherein said visualization template comprises multiple nodes, each node having one or more graphical attributes, wherein each node representative of a corresponding stage of said multiple stages; assign each of one or more of said one or more graphical attributes of each of said nodes to a corresponding one of said one or more parameters of said corresponding stage; and visualize one or more differences between said data clusters by generating at least one instance of said visualization template, said at least one instance representative of and corresponding to at least two of said data clusters, wherein each of said at least one instance representative of and corresponding to at least one of said data clusters, and wherein in said at least one instance, each of said assigned one or more of said one or more graphical attributes of each node represent a value of said corresponding one of said one or more parameters, said value relating to said corresponding stage of said at least one corresponding data cluster.

In some embodiments, the method of further comprises using said at least one hardware processor for: defining one of said multiple data clusters as a reference data cluster, and the remainder of said multiple data clusters as non-reference data clusters; determining a reference value for each of said assigned one or more graphical attributes, wherein said reference value is associated with said value of the corresponding parameter of said reference data cluster, wherein said generated at least one instance of said visualization template representative of and corresponding to said reference data cluster and at least one of said non-reference data clusters, and wherein generating at least one instance of said visualization template comprises: generating at least one non-reference instance of said visualization template, each of said at least one non-reference instance corresponding to and representative of one of said non-reference data clusters, wherein, in said at least one instance, each one or more of said one or more assigned graphical attributes receives a value based on the value of the corresponding parameter of the corresponding non-reference data cluster and with respect to said reference value and said value of said corresponding parameter associated with said reference value.

In some embodiments, said visualizing of one or more differences between said data clusters further comprises generating a reference instance of said visualization template representative of said reference data cluster, wherein in said instance, each of said one or more assigned graphical attributes receives said reference value.

In some embodiments, said defining one of said multiple data clusters as a reference data cluster comprises defining the data cluster having path variations with respect to the largest amount of subjects as the reference data cluster.

In some embodiments, said defining one of said multiple data clusters as a reference data cluster is performed by a user of said method.

In some embodiments, the method further comprises using said at least one hardware processor for: constructing a reference data cluster, and defining said received multiple data clusters as non-reference data clusters; and determining a reference value for each of said assigned one or more graphical attributes, wherein said reference value is associated with said value of the corresponding parameter of said reference data cluster, wherein said generated at least one instance of said visualization template representative of and corresponding to said reference data cluster and at least one of said non-reference data clusters, and wherein generating at least one instance of said visualization template comprises generating at least one non-reference instance of said visualization template, each of said at least one non-reference instance corresponding to and representative of one of said non-reference data clusters, wherein, in said at least one instance, each one or more of said one or more assigned graphical attributes receives a value based on the value of the corresponding parameter of the corresponding non-reference data cluster and with respect to said reference value and said value of said corresponding parameter associated with said reference value.

In some embodiments, said one or more graphical attributes is selected from the group consisting of: color, area colorfulness, size, shape, transparency, borderline thickness, connector transparency, labels, internal size, internal size vs. external size, borderline thickness and borderline color In some embodiments, said at least one hardware processor is further used for generating said multiple data clusters.

In some embodiments, said at least one hardware processor is further used for displaying said at least one instance of said visualization template for a user's comparative visual review.

In some embodiments, said process is a medical treatment performed with respect to multiple patients.

In some embodiments, said program code is further executable by said at least one hardware processor to: define one of said multiple data clusters as a reference data cluster, and the remainder of said multiple data clusters as non-reference data clusters; and determine a reference value for each of said assigned one or more graphical attributes, wherein said reference value is associated with said value of the corresponding parameter of said reference data cluster, wherein said generated at least one instance of said visualization template representative of and corresponding to said reference data cluster and at least one of said non-reference data clusters, and wherein generating at least one instance of said visualization template comprises generating at least one non-reference instance of said visualization template, each of said at least one non-reference instance corresponding to and representative of one of said non-reference data clusters, wherein, in said at least one instance, each one or more of said one or more assigned graphical attributes receives a value based on the value of the corresponding parameter of the corresponding non-reference data cluster and with respect to said reference value and said value of said corresponding parameter associated with said reference value.

In some embodiments, said program code is further executable by said at least one hardware processor to generate a reference instance of said visualization template representative of said reference data cluster, wherein in said instance, each of said one or more assigned graphical attributes receives said reference value.

In some embodiments, said program code is executable by said at least one hardware processor to define one of said multiple data clusters as a reference data cluster by defining the data cluster having path variations with respect to the larger amount of subjects as the reference data cluster.

In some embodiments, said program code is executable by said at least one hardware processor to define one of said multiple data clusters as a reference data cluster by a user of said method.

In some embodiments, said program code is further executable by said at least one hardware processor to: construct a reference data cluster, and define said received multiple data clusters as non-reference data clusters; and determine a reference value for each of said assigned one or more graphical attributes, wherein said reference value is associated with said value of the corresponding parameter of said reference data cluster, wherein said generated at least one instance of said visualization template representative of and corresponding to said reference data cluster and at least one of said non-reference data clusters, and wherein generating at least one instance of said visualization template comprises generating at least one non-reference instance of said visualization template, each of said at least one non-reference instance corresponding to and representative of one of said non-reference data clusters, wherein, in said at least one instance, each one or more of said one or more assigned graphical attributes receives a value based on the value of the corresponding parameter of the corresponding non-reference data cluster and with respect to said reference value and said value of said corresponding parameter associated with said reference value.

In some embodiments, said program code is further executable by said at least one hardware processor to generate said multiple data clusters.

In some embodiments, said program code is further executable by said at least one hardware processor to display said at least one instance of said visualization template for a user's comparative visual review.

In addition to the exemplary aspects and embodiments described above, further aspects and embodiments will become apparent by reference to the figures and by study of the following detailed description.

BRIEF DESCRIPTION OF THE FIGURES

Exemplary embodiments are illustrated in referenced figures. Dimensions of components and features shown in the figures are generally chosen for convenience and clarity of presentation and are not necessarily shown to scale. The figures are listed below.

FIG. 2 shows a flow chart of visualization of clustering results of an exemplary process, constructed and operative in accordance with the method of FIG. 1;

DETAILED DESCRIPTION

Glossary

The term "subject", as referred to herein, may relate to a person or an entity that is studied or examined.

The term "process", as referred to herein, may relate to any process, procedure, routine or course of action with respect to multiple subjects, such as a medical treatment provided to patients, network routing of packages, particle movement trajectories, animal movement trajectories or relating to traffic analysis of modes of transportation.

The term "data clusters" or "clusters", as referred to herein may relate to results of running a clustering algorithm on subjects for certain process. Each single cluster represents a group of subjects with similar process pathway details.

The term "parameter", as referred to herein, may relate to a variable including a value of a type of data relating to a stage of a process. Such data may generally be statistical data. For example, if the process is a medical treatment including a stage in which a Magnetic Resonance Imaging (MRI) scan is performed, then the number of patients that did an MRI, their age mean value and the distribution of the MRI machines are parameters of this stage. The values of the parameters may be, for example, number of patients: 100 patients, age mean value: 53 years and distribution of MRI machines: 45 examinations performed by MRI machine of hospital x, 15 by MRI machine of hospital y and 30 by MRI machine of hospital z.

The term "difference" and its derivations, as referred to herein, may relate to any difference, including none.

Present embodiments provide a methodology to visually analyze and compare process flows of multiple subjects organized in clusters, by overlaying the process clustering results on the visualized process pathways. This may allow researchers to gain the ability for visual comparison of the received data clusters, which may be a vital tool, for example, in a hypothesis-generating research.

Figure 1:
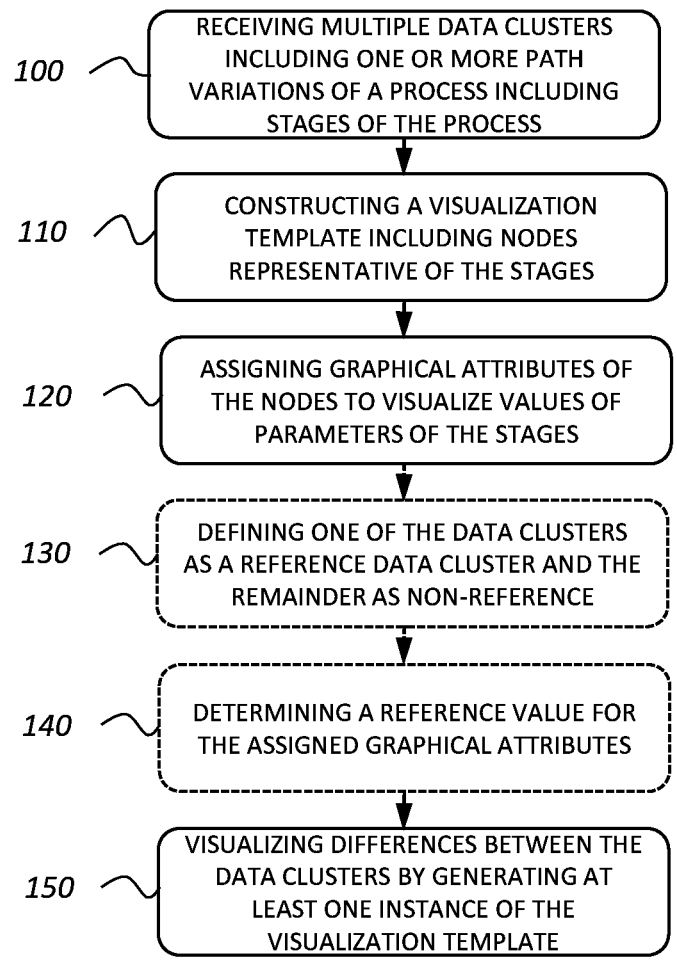
FIG. 1 shows a flowchart of a method of visual comparison of data clusters, constructed and operative in accordance with an embodiment of the disclosed technique.

Reference is now made to FIG. 1, which shows a flowchart of a method of visual comparison of data clusters, constructed and operative in accordance with an embodiment of the disclosed technique. The method may be implemented by a hardware processor. In a step 100, multiple data clusters including one or more path variations of a process are received. The process is performed with respect to multiple subjects. Each of the path variations includes multiple stages of the process. Each of at least some of the stages includes one or more parameters. Each parameter includes a value. The value may be a set of values. For example, if A, B, C, D and E represent the different stages of an exemplary process then the exemplary process may include two path variations. A first path variation, relating to one or more of the subjects, may include stages A, B, C and E. A second path variation, relating the other subjects, may include stages A, B, D and E.

In a step 110, a visualization template is constructed. The visualization template is representative of the path variations of the process. The visualization template includes multiple nodes, where each node represents a corresponding stage of the multiple stages of the process. Each node has one or more graphical attributes. The construction of the visualization template may be performed automatically, i.e., without involving a user, semi-automatically, i.e., partially involving the user or manually, i.e., the construction is performed by the user. The visualization template may include only some of the path variation or some of the process stages, for example, when a user is interested in some specific aspects of the process. Another example for using such a selective construction may be in case the process includes considerable amount of stages. In order to allow an effective visual representation of the process data, only data relating to the stages having the larger inter-cluster variance may be visualized. The visualization template may also include additional stages, which are not included in the data clusters, added manually by the user.

Reference is now made to FIG. 2, which shows a flow chart of visualization of clustering results of the exemplary process, constructed and operative in accordance with the method of FIG. 1. A template 200 is a visualization template of the exemplary process. Template 200 includes multiple nodes 210. Each node 210 represents a corresponding stage of the exemplary process. Template 200 represents all of the path variations of the exemplary process (i.e., assuming there are only two). The first path variation is along stages A, B, C and E of the process, indicated by arrow 220a, and the second path variation is along stages A, B, D and E of the process, indicated by arrow 220b. The nodes may be in various forms and other from ellipses, as nodes 210 shown in FIG. 2, such as circles, rhombuses etc. Different nodes may have different forms. The form of the node may be a graphical attribute of the node. The graphical attribute of the nodes may be used to visualize and emphasize data diversity, for example, between the data clusters, between stage parameters or in a data cluster. Graphical attribute of the nodes may be, for example, node size, node borderline thickness, connector (i.e., connecting between the nodes) thickness, labels, an internal node size, node area colorfulness, node borderline colorfulness, etc.

In a step 120, one or more of the graphical attributes of each node are assigned each to visualize values of a corresponding parameter of the corresponding stage. Each stage includes one or more parameters, such as number or percentage of subjects that went through this stage, mean of variance of a parameter (e.g., mean or variance of characteristics of the subjects that went through the stage), a p value of a parameter of the stage (i.e., to visualize the difference between distributions of the clusters), or other parameters relating to the specific stage. The type of a stage may be also a parameter of the stage and may be assigned with a graphical attribute such as node shape. Thus, different node shapes may refer to different stage types. For example, a node size graphical attribute may be assigned to visualize the number of subjects that went through the stage corresponding to the node. The graphical attributes may also visualize a value of a parameter and a baseline value of the parameter for comparison, and for example, by internal node size vs. external node size. Table 1, listing examples of assigning parameters to visual graphical attributes, is presented below.

TABLE 1

Examples of assigning parameters to graphical attributes

| Parameter | Exemplery Graphical attributes |
|---|---|
| Number of subjects that went through the stage | Node size; Node transparency; Borderline thickness; Connector transparency; Labels near nodes/connectors; |
| Number of subjects that went trough the stage compared to a baseline/reference value | Internal node size vs. external node size; |
| Internal mean and variance of a charactristic of subjects that went through the stage | Internal node size vs. external node size; Borderline thickness; |
| Variance from a baseline (e.g., from reference cluster) | Node area colorfulness; Splitted node - one half visualize a parameter value and another half a baseline/refernce value of the parameter; |
| Cause of internal variance in a stage | Color of the node borderline; |
| Different types of stages (e.g., mandatory or elective) | Node shape; |

In an optional step 130, one of the multiple data clusters is defined as a reference data cluster, while the remainder of the multiple data clusters is defined as non-reference data clusters. The reference data cluster may be used as a baseline cluster, which the non-reference data clusters are compared to. The reference data cluster may be defined automatically, according to a predefined criterion, such as the data cluster which includes path variations relating to the largest number of subjects or the data cluster which is most homogeneous (i.e., having the least variance) with sufficient size (i.e., relating to sufficient amount of subjects). Alternatively, the reference data cluster may be defined by a user of the method.

In an optional step 140, a reference value is determined for each of the assigned graphical attributes and associated with the value of the corresponding parameter of the reference data cluster defined in optional step 130. For example, the graphical attribute of area colorfulness is assigned to a parameter of a stage, e.g., the number of subjects that went through this stage. The reference value of the area colorfulness is determined to be grey (i.e., a value that renders the color grey). The value of this parameter of this stage in the reference data cluster is 10. Then, a number of 10 subjects that went through the stage is associated with a grey area colorfulness.

Generally, the same parameter (i.e., parameters of the same type, e.g., number of subjects that went through the stage) may be of different stages. In such a case, it is advantageous to assign the same graphical attributes to the same parameters (although relating to different stages) and/or to determine the same reference or baseline value for these parameters. Such configuration may facilitate the visualization of the inter-cluster differences to a user and may further allow visualizing differences between path variations and between stages in the same data cluster.

In a step 150, one or more differences between the data clusters are visualized by generating at least one instance of the visualization template. Each of the generated instances (i.e., one or more) represents and corresponds to at least one of the data clusters, while all of the generated instances represent at least two data clusters. Thus, if only one instance is generated, it necessarily represents at least two data clusters. In each instance, each of the assigned graphical attributes of each node represents the value of the corresponding parameter relating to the corresponding stage of the corresponding data cluster or data clusters. Differences between two or more data clusters may be visualized, including differences between all of the data clusters of a process.

With reference to FIG. 2, instance 220 and 240 are instances of visualization template 200. Instance 220 visualizes a first data cluster and instance 240 visualizes a second data cluster of the exemplary process. The graphical attribute of node size is assigned to the parameter of number of subjects that went through stage C and to the same parameter relating to stage D. The number of subjects in the first data cluster that went through stage C is smaller than the number of subjects in the second data cluster that went through stage C. Therefore, the size of node C in instance 220 is smaller than the size of node C in instance 240, by that visualizing a difference between the two data clusters. In addition, the number of subjects in the first data cluster that went through stage D is larger than the number of subjects in the second data cluster that went through stage D. Therefore, the size of node D in instance 220 is larger than the size of node D in instance 240. The difference or proportion between the size value of node C of instance 220 and the size value of node C of instance 240 may be equal to the proportion between the corresponding parameter value (i.e., the number of patients that went through stage C) of the first data cluster and of the second data cluster accordingly. Assuming that the subjects of the exemplary process are people then the graphical attribute of vertical hatching may be assigned to a parameter of mean value of the age of subjects that went through stage C and the graphical attribute of horizontal hatching may be assigned to a parameter of variance value of the age of subjects that went through stage D. Stages C and D of instance 220 show vertical and horizontal hatchings correspondingly less denser than the vertical and horizontal hatchings of stages C and D of instance 240 correspondingly. That is to visualize that the mean value of stage C of instance 220 is lower than the mean value of stage C of instance 240 and that the variance value of stage D of instance 220 is lower than the variance value of stage D of instance 240.

If visualization of differences between more than two data clusters is desired, a baseline or reference value may be determined for the parameters of the process stages in order to facilitate such comparison. One option is automatic definition of one of the provided data clusters as a reference data cluster as described in optional steps 130 and 140. Another option is to construct a reference data cluster (i.e., a virtual data cluster). Such construction may be, for example, by simulating a data cluster which includes parameters having baseline values. Such simulated data cluster may conveniently include data referring to all of the process path variations and all of the process stages. An additional option is to determine a null value (i.e., equivalent to zero) of each parameter as the baseline. A reference data cluster may be also constructed by merging data from a portion or all of the data clusters.

If a reference data cluster is defined and reference values are determined according to steps 130 and 140, then the at least one generated instance of the visualization template may represent and correspond to the reference data cluster and at least one of the non-reference data clusters. Furthermore, generating of the at least one instance of the visualization template includes generating at least one non-reference instance of the visualization template. Each of the generated non-reference instances may correspond to and represent one of the non-reference data clusters. In each of the generated non-reference instances, each of the assigned graphical attributes may receive a value based on the value of the corresponding parameter of the corresponding non-reference data cluster and with respect to the reference value and the value of said corresponding parameter associated with the reference value. In a further optional step, a reference instance of the visualization template representing the reference data cluster may be generated. In said instance, each of the assigned graphical attributes receives the determined reference value.

With reference to FIG. 2, the first data cluster of the exemplary process may be defined as a reference data cluster and the second data cluster as a non-reference data cluster. Instance 220 may be a reference instance of the visualization template representing the reference data cluster. Instance 240 may be a non-reference instance of the visualization template representing the non-reference data cluster. The values of the graphical attributes of the nodes of instance 220 are the reference values of these graphical attributes and are associated with the values of the parameters of the stages of the reference data cluster. The values of the graphical attributes of the nodes of instance 240 are determined based on the values of the corresponding parameters and with respect to the reference values of these graphical attributes and the values of the parameters associated to these reference values.

For example, the size of node A (i.e., external size) may be assigned to the number of subjects that went through stage A. The number of subjects that went through stage A of the reference data cluster is x. The number of subjects that went through stage A of the non-reference data cluster is y, where y=1.2*x. The value of the size of node A of instance 220 is determined to be z. z is therefore associated with x and z is determined to be the reference value of the node size of stage A. Thus, the external size of node A of instance 240 is determined to be 1.2z, based on the corresponding parameter value y, the reference value z and the proportion between the corresponding parameter value y and the parameter value x associated with the reference value z. Alternatively, instance 240 may be a the only generated visualization template representing both the reference data cluster and the non-reference data cluster of the exemplary process. Visualization of differences between the two clusters may be performed, for example, as shown with respect to stage A of the process. A graphical attribute of external node size vs. internal node size may be assigned to the number of subjects that went through stage A. The size of the internal node size of node A of instance 240 represents the number of subjects that went through stage A of the reference data cluster while the external node size of node A of instance 240 represents the number of subjects that went through stage A of the non-reference data cluster. In general, some or all of the nodes of a non-reference instance may be divided two halves, while one halve represents the reference data cluster and the other half the corresponding non-reference data cluster.

Generated instances of the visualization template according to the disclosed technique may be displayed for a user's comparative visual review in various manners. A user may define or select the desired manner of display. For example, all of the generated instanced may be displayed together on a single screen or only a portion of them. The instances may be displayed in sequence or in series or in both. The instances may be transparent such that one or more instances may be displayed one over the other. In such a display, instances may be united into one instance representing two or more data clusters. Each stage may be split into a pie-like representation, where each piece of pie relates to a different node representing a different cluster.

A method according to the disclosed technique may include a preliminary step of data clustering. Data relating to a process is received and clustered into multiple data clusters. The clustering may be performed according to different criterions and based on algorithms as known in the art, such as Hierarchical clustering, K-nearest neighbors (KNN) or Decision trees. The clustering may be performed, for example by gathering data relating to similar path variations into a single cluster. The clustering may be further performed to allow a clear visualization of the clusters differences by a user of the method, by considering, for example, the number of the resulted clusters and therefore the number of instances to be displayed.

In some embodiments, a graphical attribute of color, i.e., borderline color or fill color, or both, may be assigned to a parameter of each stage of a data cluster (i.e., the same color for all staged of the same data cluster), while each data cluster may be assigned a different color. The reference data cluster may be assigned with the neutral color, e.g. white. The differences between the clusters with respect to the reference data cluster may be visualized then by changing the value of area colorfulness of each color.

Path variations of a process performed with respect to subjects may not include all of the stages of the process. Such scenarios may be expressed in the data clusters as path variations including less stages (i.e., missing stages) or including empty stages, i.e., stages which does not include parameters, or stages which include empty parameters (i.e., with no values) or stages which include parameters having null values. The visualization of such missing or empty stages may be by instances not including nodes representing these stages or including empty nodes which represent these stages. Such empty nodes may not have some or all of the assigned graphical attributes or have graphical attributes having predefined null values.

A user of the method may be provided with the option to perform one or more of the steps of the method or a portion of it, and such as to define or construct a reference cluster (entirely or partially, e.g., by only selecting the reference values), determine the assigned graphical attributes, assign the graphical attributes to parameters and select the manner of display of the visualization instances. A user may be also provided with the option to select which data clusters are visualized or which parameters of each data cluster may be visualized.

The construction and generation of visualization templates of data clusters according to the disclosed technique may utilize various methods and algorithms as known in the art, such as those disclosed in U.S. Patent Application Publication No. 2003/0216939 to Bito, Yoshitaka et al.; U.S. Patent Application Publication No. 2012/0221355 to Schoenberg Ido et al.; David Koop et al., "*Visual Summaries for Graph Collections*" (http://vgc.poly.edu/~dakoop/pubs/graph-summaries.pdf); C. Plaisant, R. Mushlin, A. Snyder, J. Li, D. Heller, and B. Shneiderman, "*LifeLines: using visualization to enhance navigation and analysis of patient records.*" Proc AMIA Symp. 1998: 76-80; Y Shahar, D Goren-Bar, D Boaz, G Tahan, "*Distributed, intelligent, interactive visualization and exploration of time-oriented clinical data and their abstractions*", Artificial Intelligence in Medicine, 2006; and US Patent Application Publication No. 2013/0185231 to Baras et al.

Figure 3A:
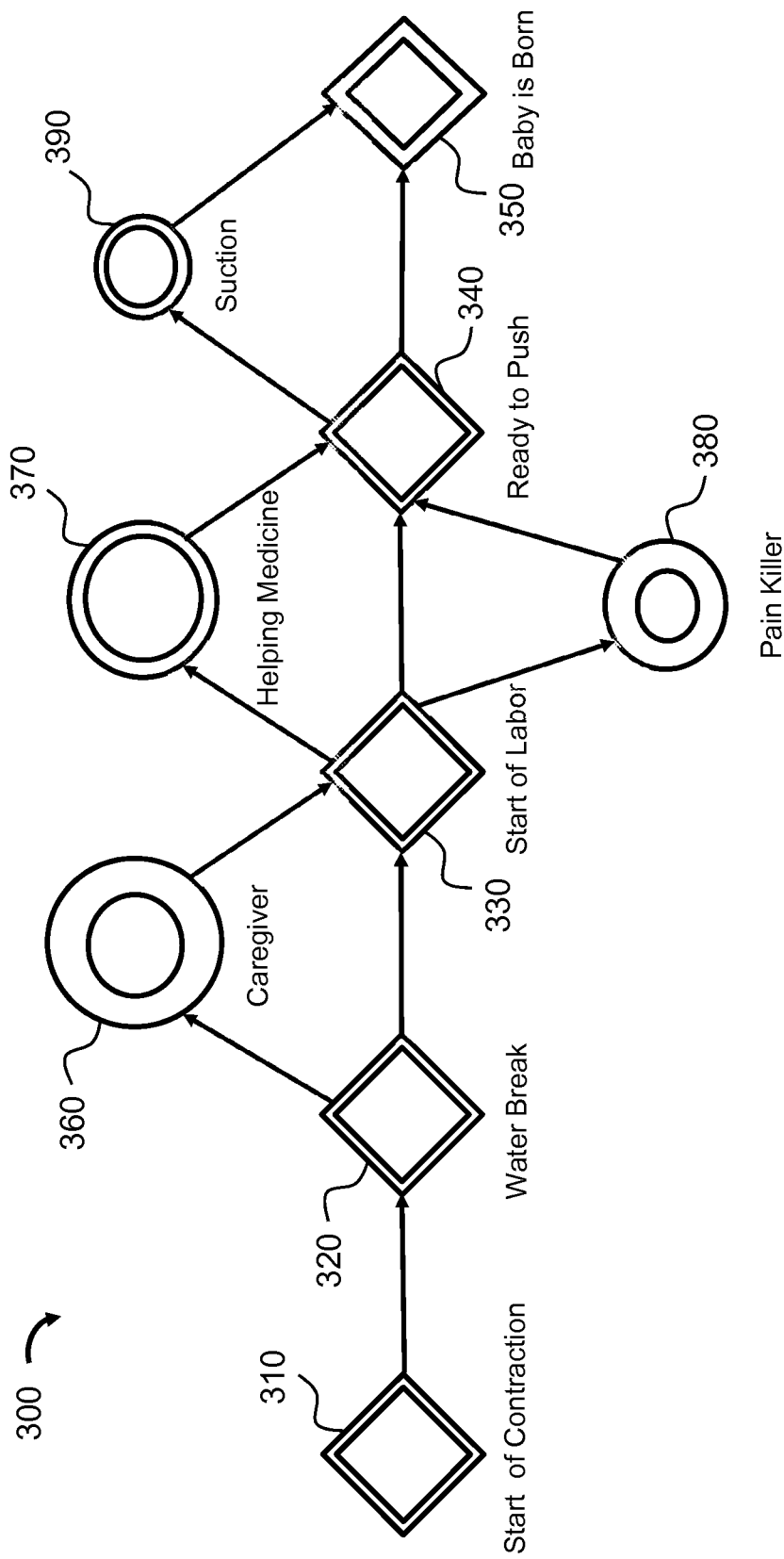
FIG. 3A shows an exemplary visualization of a reference cluster of a medical treatment, constructed and operative in accordance with yet another embodiment of the disclosed technique.
Figure 3B:
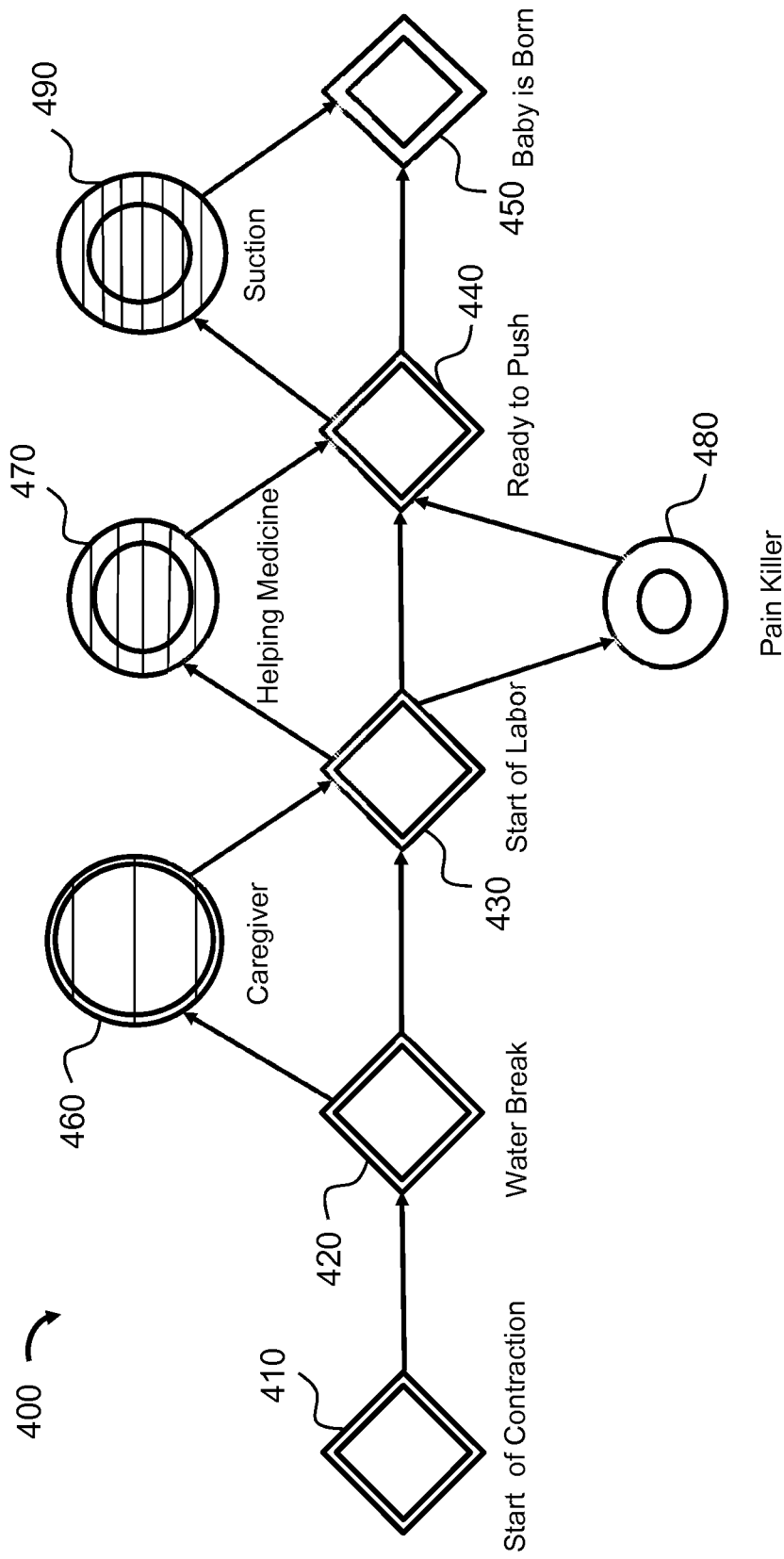
FIG. 3B shows an exemplary visualization of a non-reference cluster of the medical treatment of FIG. 3A.

Reference is now made to FIGS. 3A and 3B. FIG. 3A shows an exemplary visualization of a reference cluster of a medical treatment, constructed and operative in accordance with yet another embodiment of the disclosed technique. FIG. 3B shows an exemplary visualization of a non-reference cluster of the medical treatment of FIG. 3A. The medical treatment is a vaginal delivery treatment provided to a group of patients. Each of the patients went through the following stages of the vaginal delivery (i.e., mandatory stages): a stage of 'Start of Contractions', a stage of 'Water Break', a stage of 'Start of Labor', a stage of 'Ready to Push' and a stage of 'Baby is Born'. The following vaginal delivery stages: a stage of 'Caregiver', a stage of 'Helping Medicine', a stage of 'Pain Killer' and a stage of 'Suction' are optional, i.e., not all of the patients went through these stages. The received data (e.g., from a database or a hospital) includes two major clusters for the vaginal delivery patients. Statistical significant difference between the clusters exists in the following stages:

(i) Stage of 'Caregiver' (i.e. Physician)—The percentage of patients treated by a caregiver is equal (100%), but the distribution of personnel identities is different (p-value=$10^{-2}$);

(ii) Stage of 'Helping Medicine'—The difference in percentage of patients treated with helping medicine is insignificant (28% in reference cluster vs. 31% in non-reference cluster), but the drugs identities are different (p-value=$10^{(-3)}$); and (iii) Stage of 'Suction'—The percentage of patients that required suction procedure is different (20% in reference cluster vs. 50% in non-reference cluster; p-value=10^(−4)).

The first cluster is defined to be a reference cluster. The second cluster is defined to be a non-reference cluster. A visualization template instance 300 of FIG. 3A represents the reference cluster and a visualization template instance 400 of FIG. 3B represents the non-reference cluster. Instance 300 includes a node 310 representing the 'Start of Contraction' stage, a node 320 representing the 'Water Break' stage, a node 330 representing the 'Start of Labor' stage, a node 340 representing the 'Ready to Push' stage, a node 350 representing the 'Baby is Born' stage, a node 360 representing the 'Caregiver' stage, a node 370 representing the 'Helping Medicine' stage, a node 380 representing the 'Pain Killer' stage and a node 390 representing the 'Suction' stage. Instance 400 includes a node 410 representing the 'Start of Contraction' sage, a node 420 representing the 'Water Break' stage, a node 430 representing the 'Start of Labor' stage, a node 440 representing the 'Ready to Push' stage, a node 450 representing the 'Baby is Born' stage, a node 360 representing the 'Caregiver' stage, a node 470 representing the 'Helping Medicine' stage, a node 480 representing the 'Pain Killer' stage and a node 490 representing the 'Suction' stage.

The parameters of the reference cluster are assigned with the graphical attribute of white color. Parameters having values in the non-reference cluster, which are significantly different from their values in the reference cluster, may be assigned with the graphical attribute of another color, such as green, which is shown in FIG. 3B as horizontal hatching. Each stage type is assigned with a label. Therefore, each node is shown with a label underneath indicating the stage type. The nodes which represent the mandatory stages are assigned with a diamond-shaped node and the nodes which represent the optional stages are assigned with a circle-shaped node. The percentage of the patients going through each stage is assigned with the graphical attribute of node size. For example, nodes 310 and 410, "Start of Contraction" have size of X pixels representing 100% of patients which went through this stage, while nodes 380 and 480, "Pain_Killer", may have size of 0.3X pixels representing 30% of the patients which went through this stage. Differences between the internal and external parts of each node are assigned to visualize variance of some characteristic of the cluster subjects with respect to the specific stage. For example, in the 'Care Giver' stage, the difference between the internal and external parts of nodes 360 and 460 visualizes the variance of the care givers personnel identities. In the non-reference cluster, most of the patients had the same care giver therefore the difference between the internal and external parts of node 460 is relatively small. On the other hand, in the reference cluster, the patients were treated by different care givers hence the difference between the internal and external parts of node 360 is relatively larger. In the 'Helping Medicine' stage, the difference between the internal and external parts of nodes 370 and 470 visualizes the variance of the drugs identities. In the reference cluster, most of the patients had the same drugs therefore the difference between the internal and external parts of node 370 is relatively small. On the other hand, in the non-reference cluster, the patients were treated by different drugs hence, the difference between the internal and external parts of node 470 is relatively larger. The area colorfulness of the nodes of instance 400 visualizes the received p-value: least significant is node 460, "Caregiver", while most significant is node 490, "Suction" (shown in FIG. 3B as the density of the horizontal hatching).

Visual analysis of the visualized differences between the two data clusters by instances 300 and 400 may result, for example, in the following conclusions. It seems that most of the patients in the non-reference cluster have the same Caregiver, e.g., Dr. Smith. This is reasonable, since the variance of the care givers personnel identities as visualized by node 460, "Caregiver", of instance 400 is small, while in general there are several caregivers in the hospital (the same variance of the same stage in the reference cluster, as shown in node 360 of reference instance 300 is significant). One hypothesis explaining existing difference can be that Dr. Smith tends to use suction procedure more often than others, thus leading to different set of helping medicines as the variance of drugs identities in node 470 is larger than in node 370. Another hypothesis can be that Dr. Smith tends to use different set of helping medicines, which leads to increased amount of suction procedures. Following that, a researcher can perform additional study (i.e. interview the Dr. Smith) to confirm or reject received hypotheses and then act accordingly.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a hardware processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method comprising using at least one hardware processor for: receiving multiple data clusters each comprising one or more path variations of a process performed with respect to multiple subjects, wherein each of said one or more path variations comprises multiple stages of said process, and wherein at least some of said multiple stages each comprises one or more parameters; constructing a visualization template representative of said path variations of said process, wherein said visualization template comprises multiple nodes, each node having one or more graphical attributes, wherein each node is representative of a corresponding stage of said multiple stages; assigning each of said one or more graphical attributes of each of said nodes to a corresponding one of said one or more parameters of said corresponding stage; defining, as a reference data cluster, one of said multiple data clusters which has (a) path variations with respect to a higher number of subjects than other ones of said multiple data clusters, or (b) a least amount of variance compared to other ones of said multiple data clusters; defining, as non-reference data clusters, all of said multiple data clusters which were not defined as the reference data cluster; and visualizing one or more differences between said data clusters by generating at least one instance of said visualization template, said at least one instance of said visualization template being representative of and corresponding to at least two of said data clusters, wherein: each of said at least one instance of said visualization template is representative of and corresponding to at least one of said data clusters, in said at least one instance of said visualization template, each of said assigned one or more graphical attributes of each node represents a value of said corresponding one of said one or more parameters, said value relating to said corresponding stage of said at least one corresponding data cluster, in said at least one instance of said visualization template, each of the nodes represents said value with respect to at least some of the multiple subjects, and in said at least one instance of said visualization template, the one or more differences between said data clusters are visualized, for each of said nodes, by basing each of said assigned one or more graphical attributes on a proportion between said value in the reference data cluster and said value in the non-reference data clusters.

2. The method of claim 1, wherein said one or more graphical attributes is selected from the group consisting of: color, area colorfulness, size, shape, transparency, connector thickness, connector transparency, labels, internal size, internal size vs. external size, borderline thickness and color of borderline.

3. The method of claim 1, wherein said at least one hardware processor is further used for generating said multiple data clusters.

4. The method of claim 1, wherein said at least one hardware processor is further used for displaying said at least one instance of said visualization template for a user's comparative visual review.

5. The method of claim 1, wherein said process is a medical treatment performed with respect to multiple patients.

6. A computer program product comprising a non-transitory computer-readable storage medium having program code embodied therewith, the program code executable by at least one hardware processor to: receive multiple data clusters each comprising one or more path variations of a process performed with respect to multiple subjects, wherein each of said one or more path variations comprises multiple stages of said process, and wherein at least some of said multiple stages each comprises one or more parameters; construct a visualization template representative of said path variations of said process, wherein said visualization template comprises multiple nodes, each node having one or more graphical attributes, wherein each node is representative of a corresponding stage of said multiple stages; assign each of one or more of said one or more graphical attributes of each of said nodes to a corresponding one of said one or more parameters of said corresponding stage; and define, as a reference data cluster, one of said multiple data clusters which has (a) path variations with respect to a higher number of subjects than other ones of said multiple data clusters, or (b) a least amount of variance compared to other ones of said multiple data clusters; define, as non-reference data clusters, all of said multiple data clusters which were not defined as the reference data cluster; and visualize one or more differences between said data clusters by generating at least one instance of said visualization template, said at least one instance of said visualization template representative of and corresponding to at least two of said data clusters, wherein: each of said at least one instance of said visualization template representative of and corresponding to at least one of said data clusters, in said at least one instance, each of said assigned one or more of said one or more graphical attributes of each node represents a value of said corresponding one of said one or more parameters, said value relating to said corresponding stage of said at least one corresponding data cluster, in said at least one instance of said visualization template, each of the nodes represents said value with respect to at least some of the multiple subjects, and in said at least one instance of said visualization template, the one or more differences between said data clusters are visualized, for each of said nodes, by basing each of said assigned one or more graphical attributes on a proportion between said value in the reference data cluster and said value in the non-reference data clusters.

7. The computer program product of claim 6, wherein said one or more graphical attributes is selected from the group consisting of: color, area colorfulness, size, shape, transparency, connector thickness, connector transparency, labels, internal size, internal size vs. external size, borderline thickness and color of borderline.

8. The computer program product of claim 6, wherein said program code is further executable by said at least one hardware processor to generate said multiple data clusters.

9. The computer program product of claim 6, wherein said program code is further executable by said at least one hardware processor to display said at least one instance of said visualization template for a user's comparative visual review.

10. The computer program product of claim 6, wherein said process is a medical treatment performed with respect to multiple patients.

* * * * *